United States Patent
Miltenyi

(10) Patent No.: US 6,417,011 B1
(45) Date of Patent: *Jul. 9, 2002

(54) METHODS AND MATERIALS FOR IMPROVED HIGH GRADIENT MAGNETIC SEPARATION OF BIOLOGICAL MATERIALS

(75) Inventor: Stefan Miltenyi, Cologne (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/425,109

(22) Filed: Oct. 19, 1999

Related U.S. Application Data

(63) Continuation of application No. 08/377,774, filed on Jan. 23, 1995, now Pat. No. 6,020,210, which is a continuation-in-part of application No. 08/020,019, filed on Feb. 17, 1993, now Pat. No. 5,411,863, which is a continuation of application No. 07/291,177, filed on Dec. 28, 1988, now abandoned.

(51) Int. Cl.$^7$ ............................................. G01N 33/335
(52) U.S. Cl. .................. 436/526; 436/63; 436/501; 436/824; 436/807; 435/7.2; 435/7.21; 435/7.92; 435/283.1; 435/288.6; 435/5; 435/174; 435/173.9; 435/299; 427/2.1; 427/127; 427/212; 427/213.3; 427/214; 427/216; 427/220; 427/372.2; 422/59; 422/47; 422/49
(58) Field of Search .................. 436/526, 63, 824, 436/807, 501; 435/7.2, 7.21, 283.1, 288.6, 5, 7.92, 173.9, 174, 299; 427/2.1, 127, 212, 213.3, 214, 216, 220, 372.2; 422/59, 47, 49; 209/213, 214; 252/62.51, 302, 315.2, 315.3

(56) References Cited

U.S. PATENT DOCUMENTS

| | | | |
|---|---|---|---|
| 3,791,830 A | * 2/1974 | Abele | 96/76 |
| 3,791,930 A | * 2/1974 | Saxholm | 195/103.5 |
| 3,843,450 A | 10/1974 | Saxholm | |
| 3,970,518 A | 7/1976 | Giaever | |
| 3,981,776 A | * 9/1976 | Saxholm | 195/103.5 |
| 3,985,608 A | * 10/1976 | Saxholm | 195/127 |
| 4,018,886 A | * 4/1977 | Giaever | 424/12 |
| 4,021,308 A | * 5/1977 | Saxholm | 195/127 |
| 4,140,582 A | * 2/1979 | Saxholm | 195/127 |
| 4,213,825 A | * 7/1980 | Saxholm | 435/291 |
| 4,230,685 A | * 10/1980 | Senyei et al. | 424/12 |
| 4,324,859 A | 4/1982 | Saxholm | |
| 4,371,624 A | 2/1983 | Saxholm | |
| 4,375,407 A | * 3/1983 | Kronick | 209/8 |
| 4,432,873 A | * 2/1984 | Schuster | 210/223 |
| 4,452,773 A | * 6/1984 | Molday | 424/1.1 |
| 4,526,681 A | * 7/1985 | Friedlaender et al. | 209/214 |

(List continued on next page.)

FOREIGN PATENT DOCUMENTS

| DE | 3720844 A1 | 1/1989 |
|---|---|---|
| WO | WO87/01607 | 3/1987 |

OTHER PUBLICATIONS

Molday et al., (1977) "Application of magnetic microspheres in labelling and separation of cells." *Nature*, vol. 268:437–438.

(List continued on next page.)

Primary Examiner—Christopher L. Chin
Assistant Examiner—Pensee T. Do
(74) Attorney, Agent, or Firm—Alan W. Cannon; Bozicevic, Field & Francis LLP

(57) ABSTRACT

Improvements in the existing procedures and materials for conduct of high gradient magnetic separation (HGMS) are disclosed. The use of plastic coated matrices especially small spheres or balls which form superior magnetic gradient-intensifying supports are disclosed, along with improved methods and apparatus to conduct HGMS. The selection of small spheres in combination with the coating provides for uniform matrices of high stability.

26 Claims, 2 Drawing Sheets

U.S. PATENT DOCUMENTS

| | | | | |
|---|---|---|---|---|
| 4,539,040 A | * | 9/1985 | Mawardi | 75/1 |
| 4,544,482 A | * | 10/1985 | Rupp | 210/222 |
| 4,554,088 A | * | 11/1985 | Whitehead et al. | 252/62 |
| 4,560,484 A | * | 12/1985 | Friedlaender et al. | 210/796 |
| 4,591,556 A | | 5/1986 | Saxholm | |
| 4,657,868 A | | 4/1987 | Saxholm | |
| 4,664,796 A | * | 5/1987 | Graham et al. | 210/222 |
| 4,738,773 A | * | 4/1988 | Müller-Ruchholtz et al. | 209/214 |
| 4,770,183 A | * | 9/1988 | Groman et al. | 128/654 |
| 4,992,377 A | | 2/1991 | Saxholm | |
| 5,385,707 A | * | 1/1995 | Miltneyi et al. | 422/69 |
| 5,411,863 A | * | 5/1995 | Miltenyi | 435/6 |
| 5,465,849 A | * | 11/1995 | Wada et al. | 209/214 |
| 5,543,289 A | * | 8/1996 | Miltenyi | 435/2 |
| 5,693,539 A | * | 12/1997 | Miltenyi et al. | 436/526 |
| 6,020,210 A | * | 2/2000 | Miltenyi | 436/526 |

OTHER PUBLICATIONS

Kronick et al., (1978) "Magnetic microspheres prepared by redox polymerization used in a cell separation based on gangliosides." *Science*, vol. 200:1074–1076.

Widder et al. (1979) "Magnetic microspheres: synthesis of a novel parenteral drug carrier." *J. Pharm. Sci.* vol. 68:79–82.

Molday et al., (1982) "Immunospecific ferromagnetic iron-dextran reagents for the labeling and magnetic separation of cells." *J. Immunol. Methods* 52:353–367.

Molday et al., (1984) "Separation of cells labeled with immunospecific iron dextran microspheres using high gradient magnetic chromatography." *FEBS Lett.* 170:232–238.

Dialog.RTM. Derwent World Patent Index (File 351) English abstract and patent family data corresponding to EP 0284549 (Sep. 28, 1988).

Partial English translation (abstract) of German Patent Publication No. 734137 (Apr. 8, 1943).

* cited by examiner

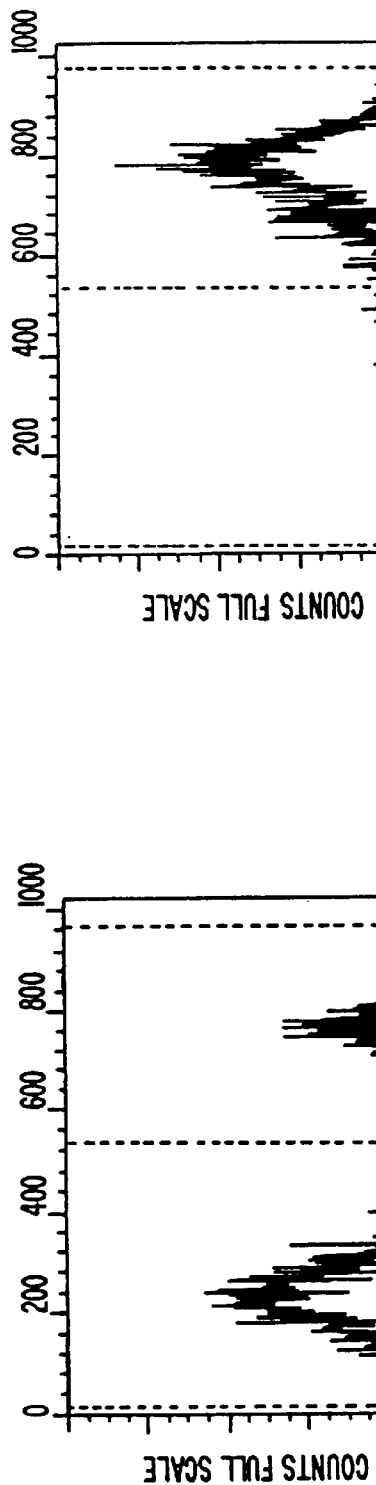

METHODS AND MATERIALS FOR IMPROVED HIGH GRADIENT MAGNETIC SEPARATION OF BIOLOGICAL MATERIALS

BACKGROUND OF THE APPLICATION

This is a continuation of pending application Ser. No. 08/377,774, filed Jan. 23, 1995 allowed, now U.S. Pat. No. 6,020,210 which is a continuation-in-part application of pending application Ser. No. 08/020,019, filed Feb. 17, 1993, now U.S. Pat. No. 5,411,863, which is a continuation application of application Ser. No. 07/291,177, filed Dec. 28, 1988, now abandoned.

TECHNICAL FIELD

The invention relates to the application of high gradient magnetic separation (HGMS) to the separation of biological cells, organelles and other biological materials. Specifically, the invention relates to improvements in particle compositions for association with the subject materials, to improvements in matrices useful in the separation apparatus, to improved separation methods, and to methods to employ magnetic fluids in such separations.

BACKGROUND ART

High gradient magnetic separation refers to a procedure for selectively retaining magnetic materials in a chamber or column disposed in a magnetic field. This. technique can also be applied to non-magnetic targets labeled with magnetic particles. In one application of this technique a target material, typically a biological material, is labeled by attaching the target material to a magnetic particle. The attachment is generally through association of the target material with a specific binding partner which is conjugated to a coating on the particle which provides a functional group for the conjugation. The material of interest, thus coupled to a magnetic "label", is suspended in a fluid which is then applied to the chamber. In the presence of a magnetic gradient supplied across the chamber, the magnetically labeled target is retained in the chamber; if the chamber contains a matrix, it becomes associated with the matrix. Materials which do not have magnetic labels pass through the chamber. The retained materials can then be eluted by changing the strength of, or by eliminating, the magnetic field. The magnetic field can be supplied either by a permanent magnet or by an electromagnet. The selectivity for a desired target material is supplied by the specific binding-partner conjugated to the magnetic particle. The chamber across which the magnetic field is applied is often provided with a matrix of a material of suitable magnetic susceptibility to induce a high magnetic field gradient locally in the chamber in volumes close to the surface of the matrix. This permits the retention of fairly weakly magnetized particles, and the approach is referred to as high gradient magnetic separation (HGMS).

U.S. Pat. No. 4,452,773 ('773) describes the preparation of magnetic iron-dextran microspheres and provides a summary of art describing the various means of preparation of particles suitable for attachment to biological materials. As long ago as 1977, preparation of colloidal iron oxide, gamma-irradiated in the presence of hydrophilic and hydrophobic methacrylate monomers, to provide particles for attachment to biological targets through coupling to immunoglobulin was described (Rembaum, A., et al., *Nature* (1977) 268:437–438. Various other preparations of magnetic microspheres of various sizes were described by Kronick, P. L., et al, *Science* (1978) 200:1074–1076 and Widder, K., et al, *J Pharm Sci* (1979) 68:79–82 and in U.S. Pat. Nos. 3,970,518 and 4,018,886. Particles as large as 100 u have been used. All of these preparations are characterized in the '773 patent as unsatisfactory for general application to HGMS for biological materials for one reason or another.

U.S. Pat. No. 4,230,685 describes an improvement in attaching specific binding agents to the magnetic particles wherein a particle coated with an acrylate polymer or a polysaccharide can be linked through, for example, glutaraldehyde to a preparation of protein A which can then selectively bind antibodies through the Fc portion, leaving the immunoreactive Fab regions exposed. Albumin, rather than polyacrylamide or polysaccharides, is the preferred matrix. A wide size range of particles is disclosed.

In the case of the particles prepared as described in '773, particles of 100–700 angstroms, particularly 300–400 angstroms are intended to be prepared; many of the particles are thus colloidal, and are ferromagnetic with a coating of dextran. The resulting particles are described and claimed as discrete colloidal size particles having a ferromagnetic iron oxide core coated with a polysaccharide derivative having pendant functional groups provided by periodate oxidation. These particles are prepared by mixing an aqueous solution of a ferrous and ferric salt with a solution of the polysaccharide or polysaccharide derivative. After this mixing, alkali is added to cause the formation of the magnetic iron oxide particles to which the polysaccharide or derivative attaches. The resulting particles are separated from excess dextran using gel filtration chromatography. A single peak containing the entire size range of particles is obtained. The polysaccharide is then treated to provide the needed functional groups for conjugation to an immunospecific or other specific binding reagent.

Other polymeric coatings for magnetic particles used in HGMS, or for other biological applications such as NMR imaging, are found in PCT application WO85/04330.

In theory, several types of magnetic particles could be prepared: ferromagnetic particles, superparamagnetic particles and paramagnetic particles. Methods to prepare superparamagnetic particles are described in U.S. Pat. No. 4,770,183. With respect to terminology, as is the general usage in the art:

"Diamagnetic" as used herein, and as a first approximation, refers to materials which do not acquire magnetic properties even in the presence of a magnetic field, i.e., they have no appreciable magnetic susceptibility.

"Paramagnetic" materials have only a weak magnetic susceptibility and when the field is removed quickly lose their weak magnetism. They are characterized by containing unpaired electrons which are not coupled to each other through an organized matrix. Paramagnetic materials can be ions in solution or gases, but can also exist in organized particulate form.

"Ferromagnetic" materials are strongly susceptible to magnetic fields and are capable of retaining magnetic properties when the field is removed. Ferromagnetism occurs only when unpaired electrons in the material are contained in a crystalline lattice thus permitting coupling of the unpaired electrons. Ferromagnetic particles with permanent magnetization have considerable disadvantages for application to biological material separation since suspension of these particles easily aggregate due to their high magnetic attraction for each other.

"Superparamagnetic" materials are highly magnetically susceptible—i.e., they become strongly magnetic when placed in a magnetic field, but, like paramagnetic materials, rapidly lose their magnetism. Superparamagnetism occurs in ferromagnetic materials when the crystal diameter is decreased to less than a critical value. Superparamagnetic particles are preferred in HGMS.

Although the above-mentioned definitions are used for convenience, it will immediately be apparent that there is a continuum of properties between paramagnetic, superparamagnetic, and ferromagnetic, depending on crystal size and particle composition. Thus, these terms are used only for convenience, and "superparamagnetic" is intended to include a range of magnetic properties between the two designated extremes.

The extent of magnetization which is acquired by a particle is a function of its magnetic susceptibility and the applied magnetic field. The magnetization is a function of the resulting magnetic moment and of the volume of the particle. The higher the magnetic moment and the smaller the volume, the higher the magnetization.

Various forms of apparatus for use in HGMS have also been described. Early workers, as exemplified by Molday, R. S., et al, *J Immunol Meth* (1982) 52:353–367, used simply a tuberculin syringe body across which a magnetic gradient was applied. U.S. Pat. No. 4,738,773 describes a separation apparatus which employs helical hollow tubing made either of stainless steel or Teflon for example, wherein the helices are placed in an applied magnetic field. Graham, M. D., WO87/01607 and Graham, M. D., et al, U.S. Pat. No. 4,664,796 describe more complex configurations in which the position of the magnetic field can be varied across the separation column. A feature of the Graham et al apparatus (which has been used by others, also) is the inclusion of a matrix which intensifies the localized magnetic gradient as the fluid passes through the interstices of the matrix; this is a necessity for separation of weakly magnetic materials, such as paramagnetic red blood cells. Complex protocols for retention and elution which involve alteration of the position of the magnetic field and alteration of the velocity or viscosity of the carrier fluid are also described. The matrix itself is described as constructed of magnetic wires, fibers, spheres and so forth. Such a description would include, for example, steel wool.

Kronick, U.S. Pat. No. 4,375,407 ('407) describes a device for HGMS where the fluid, which contains the particles to be separated, is passed through a filamentary material that has been coated with a hydrogel polymer. According to the disclosure in '407, advantage is taken of the strong magnetic forces produced by the high field gradients at the edges of the filaments which permit particles of even very weak magnetic material to be retained. This advantage of providing a filamentous matrix had been recognized in chemical processing and related methodologies, but, in separations involving biological materials, the filament retains biological entities nonspecifically and furthermore damages them. In part, damage to biological materials in the systems is due to the oxidation (corrosion) of the matrix and the resulting ions in solution, or to the chemical alteration of the magnetic particles to which the biological materials are conjugated. The propensity of the matrices to corrode is intensified in physiological solutions containing saline.

The hydrogel polymer in '407 is for the purpose of overcoming some of these drawbacks. The hydrogel polymer is defined as a polymer which imbibes or absorbs water to the extent of at least 30% of the weight of the polymer. Exemplified are hydrophilic acrylic polymers (advantageously having functional groups for further derivatization). The use of anything other than a hydrophilic hydrogel is indicated to be disadvantageous as resulting in nonspecific adsorption of biological materials. Nevertheless, it is clear that hydrogels cannot protect the filaments of the matrix from corrosion or the passage of the ions formed by this corrosion through the hydrogel into the fluid being passed through the interstices. The function of the hydrogel appears to be associated mainly with elimination of non-specific binding. Other features of the separation apparatus are standard.

The art thus provides methods for effecting HGMS which are useful, but far from optimal. The present invention is directed to methods and materials which result in more versatile and more effective magnetic separations of biological materials.

DISCLOSURE OF THE INVENTION

The invention provides improvements in the high gradient magnetic separation apparatus and methods and biological material labeling methods. Application of the invention improvements to isolation of particular cells, proteins, polysaccharides, and other biological materials or other materials which are magnetic or are capable of a specific binding interaction to associate with a magnetic label results in more specific and more efficient means to isolate these materials.

One set of improvements is directed to the apparatus used to conduct separation, and specifically to the column or chamber in which separation occurs. In typical HGMS procedures, the fluid containing the magnetic and nonmagnetic particles is passed through a vessel or column which is disposed in a magnetic gradient. In desirable ways to conduct such separations, the vessel is filled with a matrix which is capable of creating high magnetic gradients in the neighborhood of its surface. While the strength of the magnetic field imposed on the particles determines their magnetization, their retention is a function of the strength of the magnetic gradient. Magnetized particles are retained by high magnetic gradients. Typical matrices are made from filamentous or particulate metal components such as steel wool, wires or filaments or particulates or grids.

In the development of matrices made from differently shaped materials small speres or beads proved to be most predictable in their characteristics as well as most stable in their structure. The symmetric shape allows to predict through-put of liquids even after coating of the assembled metal components. A change on through-put of liquids can easily correlated with the amount of retained material.

The applied coating adds after finishing adds mechanical stability to the matrix. This stability is of importance during handling of a matrix and when changing the magnetic field in the HGMS apparatus.

The invention provides a method of coating such matrices which both efficiently and effectively protects biological materials subjected to passage through the matrix from damage which would be caused by exposure of these materials to the metallic surface. The coating on the matrix effectively prevents the corrosion of the metallic surfaces and prevents the passage of any ions which might form at the surface into the surrounding fluid. Furthermore, the impermeable coating provided by the invention adds physical stability to the matrix.

Other improvements are directed to the overall configuration of the apparatus which comprises a high intensity permanent magnet disposed laterally across a separation chamber, which separation chamber includes an inlet means and an outlet means, wherein the outlet means contains a means for constricting the flow of fluid.

Thus, in one aspect, the invention is directed to an apparatus for conducting HGMS which comprises a high intensity permanent magnet between the poles of which is disposed a chamber having an inlet means at the top of said chamber and an outlet means at the bottom of said chamber, wherein the outlet means includes a means for constricting the flow of fluid out of the chamber.

In another aspect, the invention is directed to a method of coating a magnetic gradient-creating matrix, which method comprises treating said matrix with a liquid which contains plastic polymer or which contains a monomer capable of forming a solid coating, removing excess amounts of the liquid, and permitting the solid impermeable coating to form. The resulting coating will contain <30% water by weight. The coating may be a preformed polymer which is adhered to the matrix by drying and removal of the carrier liquid, or by cross-linking catalyzed by a suitable reagent, or may be formed by polymerization of a monomer in situ. This process can be conducted with the matrix in a preparation vessel, or with the matrix already disposed in the chamber of the apparatus for HGMS. In related aspects, the invention is directed to the resulting polymer-coated matrix and the apparatus containing the coated matrix.

With regard to methods and materials for magnetic labeling of materials to be separated, polysaccharide coated superparamagnetic particles of colloidal size are provided, wherein the coating can be conjugated to moieties which confer on the particle specificity for binding to the target material whose isolation is desired. A particularly preferred coating is comprised of polysaccharide. Accordingly, in another aspect, the invention is directed to a method of preparing superparamagnetic colloidal coated particles for use in HGMS, which process comprises precipitating magnetic iron oxide (from ferric/ferrous ion solution) in colloidal form, treating the colloid with a suitable coating material, such as a polysaccharide. The generation of the magnetic iron oxide particles and providing them with a polysaccharide or other organic coating can be simultaneous or sequential. The process also includes selecting a subpopulation of the resulting coated particles which have desired magnetic properties. The separation is conducted using the HGMS technique itself. Another aspect of the invention is the conduct of separation based on intensity of magnetization.

In a related aspect, the invention is directed to the particles prepared as described, and to such particles derivatized to a specificity-conferring moiety as well as such particles further associated with target biological material. In another aspect, the invention is directed to superparamagnetic coated particles of uniform intensity of magnetization, either unconjugated or conjugated to a specific binding moiety, regardless of the method of preparation.

In other aspects, the invention is directed to methods to separate biological materials using the matrix, apparatus, and particles of the invention. The separation method can be used to isolate a particular magnetically labeled material, or can effect a pseudochromatographic separation of mixtures.

BRIEF DESCRIPTION OF THE DRAWINGS

FIG. 2A–2C shows HGMS separation of cells having Thy-1 antigens from cells which do not.

MODES OF CARRYING OUT THE INVENTION

Definitions

Figure 1:
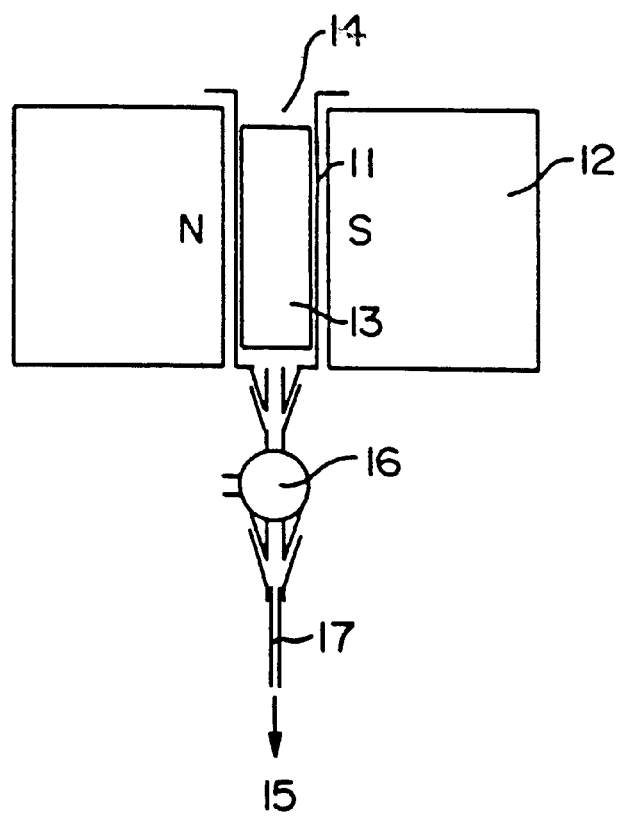
FIG. 1 shows a schematic diagram of the apparatus of the invention in a preferred embodiment.
Figure 1:
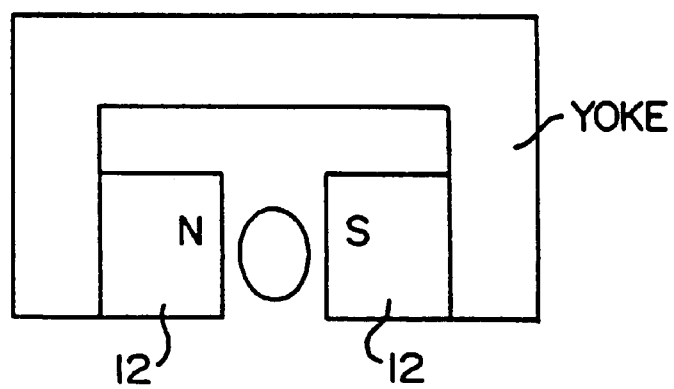

As used herein, "superparamagnetic" refers to materials whose properties lie on the continuum between paramagnetism and ferromagnetism. As explained in the background section, the degree of magnetization achievable by a particle in the presence of a magnetic field has partly to do with the coupling of the unpaired electrons in the material with each other. Thus, paramagnetic particles are those which have a minimum of coupling among the unpaired electrons such as those in the iron of the hemoglobin contained in them; ferromagnetic particles are those where the iron atoms (or other magnetic transition metal) are highly coupled. Superparamagnetic materials occupy the range between these extremes.

By "impermeable coating", as it relates to the coating provided to the matrix of the invention, is meant a polymeric coating which contains substantially less than 30% water by weight, and is coated to the matrix as a result of passive application, cross-linking or polymerization of a relatively hydrophobic polymer or copolymer. A variety of materials can be used to form impermeable membranes, as is generally understood in the art. Suitable polymers include polystyrenes, polyacrylamides, polyetherurethanes, polysulfones, fluoronated or chlorinated polymers such as polyvinyl chloride, polyethylenes and polypropylenes, polycarbonates and polyesters. Other polymers include polyolefins such as polybutadiene, polydichlorobutadiene, polyisoprene, polychloroprene, polyvinylidene halides, polyvinylidene carbonate, and polyfluorinated ethylenes. A number of copolymers, including styrene/butadiene, alpha-methyl styrene/dimethyl siloxane, or other polysiloxanes can be used. Included among these are polydimethyl siloxane, polyphenylmethyl siloxane, and polytrifluoropropylmethyl siloxane. Other alternatives include polyacrylonitriles or acrylonitrile-containing polymers such as poly alpha-acrylanitrile copolymers, alkyd or terpenoid resins, and polyalkylene polysulfonates. Any polymeric material which is capable of forming an impermeable coating which contains substantially less than 30% by weight of water, and which does not permit the passage of ions is included within the scope of the invention.

By "gradient-intensifying matrix" is meant a magnetically susceptible material which typically has a large surface area in comparison to the volume of the separation chamber which serves to create additional gradient in its vicinity so as to retain magnetized particles in a volume defined by the gradient close to its surface. The matrix thus behaves in a manner analogous to the adsorption support in an affinity chromatography column wherein the most magnetized particles are most attracted to the neighborhood of the matrix, and these more highly magnetized particles can displace particles of lower magnetization from the surface.

By "magnetization" of the particles of the invention is meant their magnetic moment per volume. Typically, magnetization is measured in Bohr magnetons per unit volume. For the superparamagnetic particles of the invention, magnetization is acquired only in the presence of an externally applied magnetic field. Thus, in referring to particles of homogeneous magnetization, it is assumed that an identical magnetic field for all particles in the mixture is imposed. As the extent of magnetization depends on the externally applied magnetic field and the magnetic susceptibility of the particles (the susceptibility is magnetization/imposed field), it also follows that these particles will have homogeneous magnetic (volume) susceptibilities.

It should be noted that the labeled biological material may have various ratios of volume or numbers with regard to the particles of the invention. Thus, for large biological materials such as cells, a multiplicity of the invention particles may be attached to the cellular surface. On the other hand, if the material to be tagged is a single molecule, a multiplicity of such molecules may reside on a single particle. Attaching a large nonmagnetic material, such as a cell to a label alters the magnetic characteristics of the label to some extent due to the increased volume of the complex. Conversely, attaching a multiplicity of magnetic labels to a cell enhances the overall magnetization associated with the cell. The total magnetization of the labeled target in a magnetic field will thus depend on the individual magnetic moment of the particles, the size (volume) of the resulting labeled complex, and the number of magnetized particles per labeled complex.

Preparation of the Particles

The superparamagnetic particles of the invention are initially prepared in a range of sizes which result in variations in their abilities to acquire magnetic properties upon exposure to a magnetic field. The magnetic particles themselves are collections of magnetic iron oxide microcrystal of 50–600 angstroms which are aggregated into particles of colloidal size—i.e., approximately 100–2000 angstroms in diameter, preferably around 400–1000 angstroms in diameter. By sorting the mixture of particles into subfractions which have uniform magnetization, compositions having homogeneous properties with respect to ability to be retained in the magnetic field can be obtained. Use of particles of such homogeneity has the advantage of effecting a sharp separation peak in chromatographic procedure, as well as the potential for labeling various components in a mixture with sets of particles of differing magnetic susceptibilities to permit chromatographic separation of these components. The particles can also be separated according to size. The desirable size will depend on the nature of the separation desired. It may be desirable to prepare relatively small particles for multiple labeling of a cell, e.g., in order to resolve the number of antigens on a cell, or relatively large particles for separation of a multiplicity of molecules of a single substance. It is, in any event, of interest to obtain sets of particles with uniform magnetizations, i.e., which become equally magnetized in the presence of the same externally applied magnetic field.

In general, the superparamagnetic particles themselves are prepared by an important modification of the method described in U.S. Pat. No. 4,452,773. Solutions containing ferric and ferrous salts in a molar ratio of about 2:1–1.5:1 along with a suitable quantity of coating material, typically a weight of polysaccharide approximately 5–20 times the weight of iron salts in solution are stirred and heated to about 40° C. Preferred coatings to be used in this process are polysaccharide or protein coatings. A preferred polysaccharide coating is dextran. The mixture is then titrated to basic pH with sodium hydroxide by dropwise addition over a period of about 1 hour. The use of sodium hydroxide or other strong base rather than the ammonium hydroxide of the reference is helpful in preventing nonspecific binding in the finished particles. Furthermore, the addition of base at elevated temperatures assists in the formation of the desired size particles. The coating material can be included, as above, in the magnetic oxide forming preparation, or can be added after the colloidal oxide particles are formed. After neutralization with acid, aggregates are removed by any convenient means such as filtration or centrifugation and the magnetic particles removed from the uncomplexed coating material by washing in a high gradient magnetic field.

The superparamagnetic particles can be subjected to HGMS at any stage of this preparation process—before or after coating and before or after size separation. The prepared particles are applied to the HGMS apparatus described below, or any alternative standard HGMS apparatus and fractionated according to magnetization (i.e., magnetic susceptibility). In one procedure, the mixture is applied to the HGMS column, containing matrix, at a very high magnetic field strength so that virtually all of the particles are retained. The particles are then eluted by gradual reduction of the magnetic field across the column. Fractions are collected at arbitrary intervals resulting in the preparation of a series of compositions each having a desired degree of homogeneity of magnetization. In a preferred procedure, however, the mixture of particles is segregated by overloading an HGMS matrix with the preparation. In this case, only the most highly magnetized particles—i.e., those having the highest magnetization—are retained, while the remainder of the preparation flows through the matrix. The retained materials can then be eluted by removing the imposed magnetic field. By properly balancing the amount of surface area of the matrix and quantity of particles, any arbitrary fraction of the highest magnetization particles in the distribution resulting from the initial preparation can be retained. Desirably, in order to obtain good homogeneity and high magnetization and susceptibility, a sufficiently small amount of matrix should be used so that the majority of the particles, about 80%, preferably about 90%, of the particles, pass through the matrix.

Thus, in a typical preparation resulting in a Gaussian distribution of magnetization, only a small portion of the upper "tail" is retained and recovered. However, additional fractions of lower magnetization can be obtained by recycling the flow-through through a clean matrix. Elution from this matrix can be had by removing the magnetic field, or by displacement with the higher magnetization fraction.

These compositions are then useful for labeling biological materials to permit the isolation of these materials either from unconjugated contaminating materials or from other materials in a mixture which are conjugated to other particle compositions of different magnetizations.

Because suspensions of uniform and very high magnetization can be obtained using the method of the invention, the process of labeling the targeted biological material can be conducted at a much higher dilution and in a much shorter time than in the processes found in the art. Because of these modifications, nonspecific binding of materials to the particles is minimized. In the illustration below, retention rates for the desired cells are several tenfold those possible in the separations described, for example, in U.S. Pat. No. 4,452,773 (supra).

In conjugating the coated particles to a specific binding moiety which is directed to a target biological material, the polysaccharide or other coating is suitably derivatized to provide functional groups for conjugation to the specific binding moiety. A variety of such modifications is known in the art. For example, polysaccharides are conveniently oxidized using periodate to provide aldehyde functional groups which can then be conjugated to amino substituents on a proteinaceous binding moiety, or can be reacted with CNBr to provide this functionality. Protein coatings can be linked to targets through side chain amino or sulfhydryl groups.

As used herein, "specific binding moiety" or "specific binding partner" means a substance which is specifically reactive with a particular target biological material to the exclusion of other biological materials. The most commonly used specific binding moiety is an immunoglobulin or immunoreactive fragment thereof. However, other forms of specific binding moieties, such as avidin/biotin or receptor/ligand are included within the scope of the invention. Many specific binding moieties are proteins, and can conveniently be conjugated to the coating through amino groups. However, a variety of other methods of conjugation are available, and a large variety of homobifunctional and heterobifunctional linkers useful in effecting such conjugation are available, for example, from Pierce Chemical Co. Linkers can be of specified lengths also, to effect a specific separation between the particle and target. Techniques for conjugation of specific binding moieties to polysaccharide solid supports are well known in the art and have been applied extensively to specific binding assays, notably immunoassays. Any suitable derivatization and conjugation method is contemplated by the invention.

By "target biological material" is meant any biological substrate for which a specific binding moiety (partner) can be found so as to specifically label the material. The list of suitable target materials is extensive and includes microorganisms such as protozoa, bacteria, yeast, and other fungi, cultured cells from multicelled organisms including mammalian and other vertebrate cells, viruses, and fragments of the cells and viruses. Also appropriate are organelles or suborganelles of eucaryotic cells, and aggregates or individual molecules including proteins, glycoproteins, lipoproteins, carbohydrates, lipids, and the like. Any biological material, either a single substance or an organized or amorphous aggregate of substances, having a characteristic target which is complementary to a specific binding moiety can be isolated or purified using the particles and methods of the invention.

There are thus prepared compositions of coated or uncoated superparamagnetic particles of magnetic iron oxide microspheres, said particles being of colloidal size and having magnetizations such that the value of the magnetization in the compositions varies less than 10%, preferably less than 5%, and most preferably less than 1%. Similarly, this level of homogeneity can be obtained in the coated colloidal superparamagnetic particles which have been conjugated to a specific binding moiety, which particles may be further associated with the target biological material. Compositions having this level of homogeneity of any of these superparamagnetic particles are so far unknown in the art.

Coating of the Focusing Matrix

The separation of the particles of the invention into compositions of homogeneous magnetic susceptibility is accomplished by HGMS, which is preferably conducted so as to include the improved methods and apparatus of the invention. In this separation, the matrix which is comprised of iron or steel or filaments, particles, or other finely divided magnetically susceptible metal, such as spheres and small beads, is coated by a hydrophobic plastic liquid which is converted to form an impermeable coating at the surface of the matrix. The matrix should have an adequate surface area to create sufficient magnetic field gradients in the separation chamber to permit efficient retention of magnetized particles. Typically, the matrix comprises about 0.5–10% of the total volume occupied by fluid in the separation chamber. The volume occupied by the matrix is important with respect to the volume left for retaining particles and the flow-through of liquid and not-retained particles. Using fine spheres or beads made from magnetic suszeptible metal for implementing a matrix provides for a predictable flow-through space. The nearly uniform shape of the surface of the spheres or beads creates similarely uniform magnetic gradients and thereby improves the uniform chracteristics of the retained magnetic particles.

As the matrix serves to create a high magnetic gradient locally to its surface, it is designated a "gradient-intensifying matrix". The high gradients at the surface of the matrix serve to attract the magnetic particles in the volume of fluid in the neighborhood of the surface of the matrix. The particles with higher magnetization are attracted preferentially. This is further enhanced by the use of matrix elements having the uniform curvature of the surfaces of a ball or sphere.

The coating of the matrix is performed by treating the matrix with a liquid composition which contains the materials which will form the coating. The resulting coating is to be distinguished from the hydrogels of the prior art, and are of very low or no water content. Suitable plastic coatings are already prepolymerized lacquers and other hydrophobic compositions, or are monomers capable of forming impermeable polymers or membranes. Suitable polymers include various hydrophobic polymers and copolymers, and representative examples have been set forth above. Mixtures of polymers and copolymers can also be used.

In one approach to coating the particles of the invention, the polymerized plastic is converted to liquid form through dispersion or solution in an appropriate solvent, preferably a non-aqueous solvent, or by appropriate temperature control. When in liquid form or dispersed in a carrier, the plastic is contacted with the matrix. Typically, the matrix can be disposed in the column of the apparatus and the fluid-borne or fluidized plastic poured through the column. Alternatively, the matrix and plastic fluid can be mixed and then the excess fluid removed by centrifugation or by decanting. The coated matrix is then dried to obtain a uniform film.

In an alternative approach, the prepolymerized material or partially prepolymerized material can be crosslinked when in contact with the matrix to obtain the impermeable coating. In another alternative, a solution of the monomer or monomers which will polymerize in the presence of the matrix can be used.

In any case, the coating contains substantially less than 30% by weight of water, preferably less than 10% more preferably less than 5%, and most preferably less than 1% water. The coating is essentially impermeable to ions, and thus protects the matrix from interaction with the biological materials, as well as preventing corrosion of the matrix and escape of the resulting cations, which would be damaging to the targeted substances and organelles. The finished coated matrix can be further coated, if desired, with additional materials, in particular, by a silicone coating. Any additional coating which does not interfere with the interaction of the matrix with the magnetic field for creation of surface magnetic gradient can be used.

The coating of a matrix, and especially of a matrix assembled from fine spheres or beads provides additional mechanical support to the matrix since the spheres or beads are packed prior to coating and maintain the packing structure during hardening of the coating. The finished matrix does not exhibit significant elasticity which would allow deformation of the matrix caused by the external magnetic field. A deformation of the matrix by a change in the external magnetic field may loosen retained particles and thereby change the output of the HGMS process.

Methods of Separation

The coated matrix of the invention is then employed in the conduct HGMS when disposed in a column subjected to a magnetic field, in such manner that a magnetic gradient is created in a volume of fluid close to the surface of the matrix. A preferred apparatus is shown in FIG. 1. As shown in FIG. 1, a chamber 11 filled with a gradient-intensifying matrix 13 is disposed between the poles of a magnet 12. The sample is applied to the inlet means at the top of the chamber 14 and exits at the outlet means in the lower portion of the chamber 15, through a means to constrict the flow of fluid such as the needle 16. When the magnetic field is applied, the gradient is created and suitable magnetically labeled samples are retained in the chamber.

A sample containing at least one biological material which has been associated with magnetic particles of the invention containing the appropriate specific binding moiety (or associated with other magnetic particles) is poured over the matrix in the column. The magnetic field is applied with sufficient strength to obtain a gradient which retains the magnetic particles on the surface of the matrix, but contaminating substances which have no magnetic properties flow through the column. When the flow-through containing the nonmagnetized material is removed, the retained particles are eluted by release or diminution of the magnetic field or both, as is understood in the art.

A preferred embodiment shown in FIG. 1 utilizes a permanent magnet to create the magnetic field. The magnet is sufficiently strong to create a field of about 0.5–1 Tesla, preferably about 0.6 Tesla. The magnet is constructed of a commercially available alloy of neodinium/iron/boron. Other highly magnetized materials could also be used. Indeed, an electromagnet could be substituted in less preferred embodiments. If the permanent magnet is used, the chamber must be physically removed from the field. If an electromagnet is used, the magnetic field created by the electromagnet is compensated to zero. Upon removal of the magnet field and continued flow of suspension fluid through the chamber, the retained magnetized particles are eluted from the matrix.

It is not necessary at this stage to separate in the elution pattern the particles which are associated with biological materials and those that are not. The magnetic labeling particles are readily enough removed from the associated biological materials and separated along with the unreacted particles, for example, by exposure to a magnetic field.

The geometry of the disposition of the matrix in the chamber can also be designed to provide optimum separations. Longitudinally arranged fibers of the matrix provide a smoother gradient than transversely disposed fibers. Depending on the nature of the magnetic labeling in a particular instance, one or the other of these types of geometries may be more advantageous.

In a different approach to obtaining elution, the retained particles can be eluted by supplying a magnetized fluid—i.e., a fluid containing a suspension or dispersion of particles with higher-magnetization than those which are retained. The fluid then effectively displaces the retained particles from the matrix surface and results in their flow through the outlet means, or alters the characteristics of the overall magnetic environment in the chamber.

Thus, in other methods to conduct the separation, the retention of the particles can also be affected by the presence of a suitable magnetic fluid. By adjusting the magnetization of the fluid in which the particles are suspended, and by controlling the available surface area of the matrix, only compositions containing particles of a selected magnetic susceptibility or magnetization can be retained in the column.

Because the particles can be obtained in compositions of homogeneous magnetization, mixtures of target biological materials which do not disrupt this homogeneity, for example A and B, can be separated by treating a mixture containing these materials with compositions of particles with specific binding moieties for each with differing potential magnetizations. For example, the mixture is treated with particles conjugated to anti-A which have high magnetic susceptibility and particles conjugated to anti-B which have low magnetic susceptibility. The labeled mixture is then applied to the apparatus and a magnetic field strength sufficient to retain both A and B associated magnetic particles is supplied. In elution, the magnetic field strength or the magnetization of the suspending fluid are altered so as to release particles which are associated with B but not those associated with A, thus effecting a clean separation.

The availability of compositions of particles having various homogeneous magnetizations thus permits considerably more complex separations to be made. In principle, any number of components in a biological mixture can be labeled with particles of differing magnetizations by treating each homogeneous composition of particles with a different specific binding moiety complementary to a chosen component of the mixture. Each component will then uniquely react with one representative composition of a particular magnetization. The labeled mixture, when subjected to HGMS results in a chromatographic pattern of components separated according to the magnetization of the particles with which they are conjugated. Recovery of each material from the particulate is a straightforward matter of dissociation of the immune or other specific binding complex and removal of the magnetic particles.

The following examples are intended to illustrate but not to limit the invention.

EXAMPLE 1

Preparation of Dextran-Coated Superparamagnetic Particles

Superparamagnetic particles were prepared by mixing 10 g dextran T40 (Pharmacia, Uppsala), 1.5 g ferric chloride hexahydrate, and 0.64 g ferrous chloride tetrahydrate in 20 ml water and heating to 40° C. The solution was stirred and 20 ml 4 M NaOH was added dropwise with continued stirring. The resulting particle suspension was neutralized with acetic acid, and centrifuged for 10 min at 2,000×g followed by filtration through a 0.22 uM pore-size filter (Millex GV) to remove aggregates.

Unbound dextran was removed by washing in a high gradient magnetic field (HGMF). This was performed by washing the magnetic particles in columns of ordinary household steel wool (average diameter about 30 um) which was placed in the chamber of a HGMS device shown in FIG. 1 at a strength of 0.6 Tesla. Ten ml of particle suspension were applied to a 15×40 mm column of 2 g of steel wool, and loaded column was washed with 30 ml buffer. About 90% of the particles were washed through the column. The column was then removed from the external field and the remaining 10% of the magnetic particles were eluted.

The eluted particles form a brown suspension which is stable for more than 6 months at 4° C.

EXAMPLE 2

Formation of Coated Superparamagnetic Materials Conjugated to Avidin

Four ml of the particle suspension prepared in Example 1 was buffered in 0.2 M sodium carbonate, pH 10.5, and reacted with 10 mg CNBr dissolved in acetonitrile. The reaction was continued for 10 min, and unreacted CNBr was removed by HGMF washing conducted in a manner similar to that set forth in Example 1 above. The activated particles were eluted from the HGMF column in 4 ml 0.1 M sodium bicarbonate containing 5 mg avidin. After overnight conjugation, the reaction was stopped using a 2-hour treatment with 100 mg glycine. Uncoupled avidin was then removed by HGMF washing as set forth above, and the particles were eluted in PBS with 0.01% azide, filtered through a 0.22 uM filter and stored at 4° C.

EXAMPLE 3

Derivatization of Magnetic Particles and Conjugation to Biotin

Ten ml of the magnetic particle suspension prepared in Example 1 in 0.1 M sodium carbonate was treated for 10 min with 0.5 mg CNBr, and then 20 mg diaminohexane was added and the mixture titrated to pH 8.5 with 0.5 M sodium dihydrogen phosphate. After 2 hr, unconjugated diaminohexane was removed by HGMF washing. The resulting particles are bound to the diaminohexane as a spacer. They were resuspended in 10 ml 0.1 M sodium bicarbonate and reacted with 10 mg biotin-succinimide ester dissolved in 100 ml DMSO, and the conjugation was allowed to proceed for 4 hr at room temperature. The unbound biotin was removed by HGMF washing with PBS containing 0.01% azide, and the particles were filtered through a 0.22 um filter and stored at 4° C.

EXAMPLE 4

Purification of Murine T Cells by HGMS

A sample containing $4 \times 10^8$ mouse spleen cells was incubated for 15 min with 1 ml biotinylated anti-T-cell antibody (anti-Thy-1, clone CFO-1, 50 ug/ml) and then washed and stained with 1 ml avidin FITC (50 ug/ml, Becton-Dickinson, Mountain View, Calif.) for 15 min and washed again. The T-lymphocytes are thus fluorescent stained to permit certain measurements to be made.

The stained cells were incubated for 5 min with 1 ml diluted biotin-conjugated particle suspension, as prepared in Example 3, and diluted 1:100 in PBS containing 5 mM EDTA. This dilution and timing represent a major departure from those shown in the art. The particles thus bind through biotin to the avidin at the surface of the T-cells.

The cell suspension at 108 cells/ml was applied to a 4 ml column having an inner surface of 100 cm$^2$ and a sectional surface of 1.2 cm$^2$ and a relatively high retention factor. The sample was applied to this column in a magnetic field of about 0.6 Tesla, and the cell suspension was allowed to move through the column at about 3 cm/min. The column was then washed with an additional 10 ml PBS, and the unmagnetic fraction collected.

The column was then removed from the magnetic field, and bound cells were washed off at approximately 30 cm/min to obtain the magnetic fraction.

Samples of the original, unmagnetic, and magnetic cell suspensions were stained with 0.1 ug propidium iodide to detect dead cells and analyzed for purity by flow cytometry (FACScan Cytofluorometer, Becton-Dickinson, Mountain View, Calif.). Both forward and orthogonal light scatter were measured, as well as FITC fluorescence and propidium iodide fluorescence.

In the original sample, 28% of the cells were shown to contain the anti-Thy-1 marker, as measured by fluorescence. Propidium iodide fluorescence showed that 3.5% of the cells in the sample were dead.

In the flow-through volume, only 0.08% of the cells contained the anti-Thy-1 marker, as expected; only 0.2% were dead.

In the magnetic fraction, 81% of the cells contained the anti-Thy-1 markers, and 7.5 k of these were dead. Thus, passage through the column of the sample did not result in any cell death.

These results are further summarized in FIGS. 2A–C, which show the FACScans of the original cell suspension and of the magnetic and non-magnetic portions thereof. FIG. 2A shows a FACScan of the original cell sample segregated according to fluorescence. There are two major peaks, one of high fluorescence corresponding to the cells which are readily labeled with anti-Thy-1 and a second peak representing low fluorescence of cells not readily labeled with this antibody. FIG. 2C shows the nonmagnetic fraction corresponding to the low fluorescence peak in FIG. 2A. FIG. 2B shows the profile of the eluted magnetic fraction which corresponds to the anti-Thy-labeled cells of FIG. 2A. Thus, the HGMS approach was able to separate the cells containing Thy-1 markers from those not bearing these markers without resulting in damage to the biological materials.

Because of the coating on the matrix, which had been prepared as set forth in Example 5, virtually no cell deaths occurred in the process.

EXAMPLE 5

Preparation of Coated Matrix

A 2 ml syringe having a diameter of 6.5 mm was filled with 150 mg Cr-Mo-stainless steel wool (material 1.4113S (DIN), average fiber diameter 60 um; 20 mm in length). The filling is such that the fibers are oriented in the direction of the axis of the syringe.

The steel wool was first wetted with a diluter by pulling Lesonal V83 through the matrix, and the diluter is then removed. The commercially available two-component lacquer, Lesonal K86 (Lesonal GmbH, Nurnberg, West Germany) was then passed through the matrix and washed through. The wet column was centrifuged for 1 min at 100×g to remove excess lacquer. The matrix was dried for 2 days. The water content was less than it. The inner surface was then siliconized in vacuum.

What I claim is:

1. A method of fractionating biological material from a liquid in a separation chamber, said method comprising the steps of:

providing a columnar matrix containing non-corrosive metal particulate, filaments, or a combination of particulate and filaments;

magnetizing the columnar matrix by applying a magnetic field;

applying a sample to said chamber, said sample containing biological material, a portion of said biological material being coupled to superparamagnetic particles, wherein the magnetization of the matrix is of sufficient strength to retain at least a part of said biological material coupled to superparamagnetic particles in said chamber, and allowing the remainder of said sample to pass through said chamber.

2. The method of claim 1, further comprising collecting said remainder of the sample as it passes through said chamber, wherein said remainder of the sample contains a desired biological material, an undesired fraction of the biological material having been retained in said chamber.

3. The method of claim 1, further comprising eluting said part of said sample retained in said chamber from said chamber.

4. The method of claim 3, wherein said part of said sample eluted from said chamber contains a desired biological material, an undesired fraction of the biological material having passed through said chamber in said remainder of the sample.

5. The method of claim 3, wherein said eluting comprises physically removing said chamber from the magnetic field.

6. The method of claim 3, wherein said eluting comprises compensating the magnetic field to zero.

7. The method of claim 3, wherein said eluting comprises gradual reduction of the magnetic field across said columnar matrix.

8. The method of claim 1, wherein magnetizing comprises applying said magnetic field with a permanent magnet.

9. The method of claim 1, wherein magnetizing comprises applying said magnetic field with an electromagnet.

10. The method of claim 1, wherein said sample contains at least two different biological components, each of which are bound to superparamagnetic particles, but which have different total magnetizations, said method further comprising retaining only the component with the highest total magnetization and allowing components with lower total magnetizations to pass through said chamber.

11. The method of claim 10, wherein said allowing the components with lower total magnetizations to pass through said chamber is accomplished by reducing said magnetic field by a predetermined amount.

12. The method of claim 10, wherein said at least two different biological components are bound to superparamagnetic particles having different magnetic moments.

13. The method of claim 10, wherein said at least two different biological components each have a different number of superparamagnetic particles bound to each labeled component.

14. The method of claim 1, wherein said sample contains at least two different biological components, each of which are bound to superparamagnetic particles, but which have different total magnetizations, said method further comprising retaining said at least two different biological components bound to superparamagnetic particles, and, after said allowing the remainder of said sample to pass through said chamber, eluting the component with the lowest total magnetization from said chamber.

15. The method of claim 14, wherein said eluting the component with the lowest total magnetization is accomplished by reducing said magnetic field by a predetermined amount.

16. The method of claim 14, further comprising eluting the biological component having a second weakest total magnetization.

17. The method of claim 16, further comprising continuing to stepwise elute said biological components in successive order, progressively to the component having the highest total magnetization.

18. A method of fractionating biological material from a liquid in a separation chamber, said method comprising:
providing a separation column including an inlet means, and outlet means and a separation chamber containing a non-corrosive matrix, which is permeable to liquids and magnetizable in the presence of a magnetic field;
magnetizing said non-corrosive matrix by applying a magnetic field across said separation chamber;
inputting a sample containing biological material coupled to superparamagnetic particles into said separation chamber, the magnetized, non-corrosive matrix having a sufficient magnetic strength to retain at least a part of said superparamagnetic particles in said separation chamber; and
allowing a remainder of said sample not retained by said magnetized, non-corrosive matrix to pass through said chamber.

19. The method of claim 18, wherein said non-corrosive matrix comprises filamentous or particulate metals.

20. The method of claim 19, wherein said filamentous metals are selected from the group consisting of steel wool, wires, filaments or grids.

21. The method of claim 18, wherein said non-corrosive matrix is coated with a polymer.

22. The method of claim 18, wherein said separation vessel further comprises means for constricting the flow of fluid through said separation chamber.

23. The method of claim 22, wherein said means for constricting flow comprises a needle.

24. A method of fractionating biological material from a liquid in a separation chamber, said method comprising:
providing a separation vessel including an inlet means, an outlet means a separation chamber containing a non-corrosive matrix, which is permeable to liquids and magnetizable in the presence of a magnetic field, and means for constricting the flow of fluid through said separation chamber;
magnetizing said non-corrosive matrix by applying a magnetic field across said separation chamber;
inputting a sample containing biological material coupled to superparamagnetic particles into said separation chamber, the magnetized, non-corrosive matrix having a sufficient magnetic strength to retain at least a part of said superparamagnetic particles in said separation chamber; and
allowing a remainder of said sample not retained by said magnetized, non-corrosive matrix to pass through said chamber.

25. The method of claim 24, wherein said means for constricting flow comprises a needle.

26. The method of claim 24, wherein said superparamagnetic particles are coupled to antigens; and wherein said fractionating process separates said cells in accordance with the number of antigens attached.

* * * * *